United States Patent
Wang et al.

(10) Patent No.: US 6,328,925 B1
(45) Date of Patent: Dec. 11, 2001

(54) LAMINATE CATHETER BALLOONS WITH ADDITIVE BURST STRENGTH AND METHODS FOR PREPARATION OF SAME

(75) Inventors: Lixiao Wang, Maple Grove; Jianhua Chen, Plymouth; Nao Lee, Brooklyn Park, all of MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/670,074

(22) Filed: Sep. 26, 2000

Related U.S. Application Data (62) Division of application No. 08/611,664, filed on Mar. 6, 1996, now Pat. No. 6,124,007.

(51) Int. Cl.$^7$ .............................. B29C 47/00; B29C 47/06
(52) U.S. Cl. ....................... 264/512; 264/515; 264/516; 264/209.5
(58) Field of Search ................................ 264/512, 515, 264/516, 209.5; 604/96.01; 606/194; 428/36.91, 35.2, 910

(56) References Cited

U.S. PATENT DOCUMENTS

| | | | |
|---|---|---|---|
| 4,328,056 | 5/1982 | Snooks | 156/242 |
| 4,338,942 | 7/1982 | Fogarty | 128/344 |
| 4,576,871 * | 3/1986 | Oestreich | 428/34.9 |
| 4,608,984 | 9/1986 | Fogarty | 128/344 |
| 4,702,252 | 10/1987 | Brooks et al. | 128/344 |
| 4,744,366 | 5/1988 | Jang | 128/344 |
| 4,763,654 | 8/1988 | Jang | 128/344 |
| 4,787,388 | 11/1988 | Hofmann | 128/344 |
| 4,885,194 * | 12/1989 | Tight, Jr. et al. | 428/34.9 |
| 4,963,412 | 10/1990 | Kokeguchi | 428/137 |
| 4,990,139 | 2/1991 | Jang | 604/101 |
| 4,994,033 | 2/1991 | Shockey et al. | 604/52 |
| 5,049,132 | 9/1991 | Shaffer et al. | 604/101 |
| 5,071,406 | 12/1991 | Jang | 604/96 |
| 5,096,848 | 3/1992 | Kawamura | 437/67 |
| 5,195,969 | 3/1993 | Wang et al. | 604/96 |
| 5,270,086 | 12/1993 | Hamlin | 428/35.2 |
| 5,290,306 | 3/1994 | Trotta et al. | 606/194 |

(List continued on next page.)

FOREIGN PATENT DOCUMENTS

| | | |
|---|---|---|
| 0 457 456 A1 | 11/1991 | (EP) . |
| 0 745 395 A2 | 12/1996 | (EP) . |
| 95/22367 | 8/1995 | (WO) . |
| 96/04951 | 2/1996 | (WO) . |

OTHER PUBLICATIONS

Kim, et al, "Mechanical and Transport Properties of Coextruded Films," J. Applied Polymer Science, 29, 2359–2382 (1984).

*Primary Examiner*—Rena L. Dye
(74) *Attorney, Agent, or Firm*—Vidas, Arrett & Steinkraus, P.A.

(57) ABSTRACT

A laminate balloon comprising at least two layers of separately oriented thermoplastic polymer material, which are coextensive over the body of the balloon. The two layers may be made of different polymer materials, including an underlying layer made of a low compliant, high strength polymer, such as PET, and an overlying layer of a softer and more flexible polymer material relative to the first polymer material, such as a polyester-polyether block copolymer. The balloon structures have an additive burst pressure, meaning that they are stronger than a single-layer reference balloon corresponding to the underlying polymer layer. The balloons are characterized by a combination of flexibility and surface softness which allows catheters to track down into lesions relatively easily, puncture resistance, abrasion resistance and refoldability, in addition to low compliance and high burst strength. The balloons may be prepared with generally linear or with stepped compliance profiles. Methods of preparation of such balloons are also disclosed.

13 Claims, 3 Drawing Sheets

U.S. PATENT DOCUMENTS

| | | | |
|---|---|---|---|
| 5,295,962 | 3/1994 | Crocker et al. | 604/101 |
| 5,298,300 * | 3/1994 | Hosoi et al. | 428/34.9 |
| 5,304,132 | 4/1994 | Jang | 604/96 |
| 5,304,135 | 4/1994 | Shonk | 604/101 |
| 5,306,250 | 4/1994 | March et al. | 604/104 |
| 5,342,305 | 8/1994 | Shonk | 604/101 |
| 5,344,401 | 9/1994 | Radisch et al. | 604/96 |
| 5,348,538 | 9/1994 | Wang et al. | 604/96 |
| 5,358,487 | 10/1994 | Miller | 604/96 |
| 5,447,497 | 9/1995 | Sogard et al. | 604/101 |
| 5,478,320 | 12/1995 | Trotta | 604/96 |
| 5,490,839 | 2/1996 | Wang et al. | 604/96 |
| 5,512,051 | 4/1996 | Wang et al. | 604/96 |
| 5,587,125 | 12/1996 | Roychowdhury | 264/515 |
| 5,871,468 * | 2/1999 | Kramer et al. | 604/96 |

* cited by examiner

Fig. 7

LAMINATE CATHETER BALLOONS WITH ADDITIVE BURST STRENGTH AND METHODS FOR PREPARATION OF SAME

CROSS-REFERENCE TO RELATED APPLICATIONS

This application is a Divisional application from application Ser. No. 08/611,664, filed Mar. 6, 1996, now U.S. Pat. No. 6,124,007, the contents of which is hereby incorporated by reference.

BACKGROUND OF THE INVENTION

Balloons mounted on the distal ends of catheters are widely used in medical treatment. The balloon may be used to widen a vessel into which the catheter is inserted or to force open a blocked vessel. The requirements for strength and size of the balloons vary widely depending on the balloon's intended use and the vessel size into which the catheter is inserted. Perhaps the most demanding applications for such balloons are in balloon angioplasty in which catheters are inserted for long distances into extremely small vessels and used to open stenoses of blood vessels by balloon inflation. These applications require extremely thin walled, high strength, relatively inelastic balloons of predictable inflation properties. Thin walls are necessary because the balloon's wall and waist thicknesses limit the minimum diameter of the distal end of the catheter and therefore determine the limits on vessel size treatable by the method and the ease of passage of the catheter through the vascular system. High strength is necessary because the balloon is used to push open a stenosis and so the thin wall must not burst under the high internal pressures necessary to accomplish this task. The balloon must have some elasticity so that the inflated diameter can be controlled, enabling the surgeon to vary the balloon's diameter as required to treat individual lesions, but that elasticity must be relatively low so that the diameter is easily controllable. Small variations in pressure must not cause wide variation in diameter.

The compliance characteristics of angioplasty balloon materials are described in U.S. Pat. No. 5,447,497, incorporated herein by reference. A variety of low-compliant materials have been employed in angioplasty balloons, including polypropylene, polyimides, polyamides, and polyesters, such as PET and PEN. Such low compliant materials can generally be fabricated into higher strength balloons than balloons made of more compliant materials. The use of low compliant materials, however, has been associated with a number of minor but undesirable problems, such as poor refold characteristics, pinhole development, difficulty in bonding to the catheter structure and high friction coefficient.

To address some of these problems a number of balloon structures have been proposed in which a layer of low compliant polymer material is coated or coextruded with an over or underlying layer of another polymer material less prone to one or more of the problems occasionally encountered with low compliant balloons. Exemplary of this approach are U.S. Pat. No. 5,270,086 (Hamlin), U.S. Pat. No. 5,195,969 (J. Wang, et al.) and U.S. Pat. No. 5,290,306 (Trotta, et al), which pertain to co-extruded structures and U.S. Pat. No. 5,490,839 (L. Wang, et. al) which pertains to coated balloon structures wherein the balloon coating imparts refold and soft pliable surface characteristics. The balloons of these references are unitary structures whose compliance and burst profiles are determined primarily by the non-compliant polymer layer, with little or no contribution by the second polymer layer. However, balloons made from coextruded tubes with soft polymer material on the top layer do provide rewrap, abrasion and puncture resistance, and reduced tracking resistance.

It is also known to prepare catheter balloon structures which include two separate concentrically arranged balloon elements mounted on a catheter. References which describe such structures include U.S. Pat. No. 4,608,984, in which an outer balloon element of a highly elastic material such as latex having a deflated circumference less than the diameter of the associated catheter is disclosed for use in refolding the inner working balloon after it has been inflated and deflated; and U.S. Pat. Nos. 5,447,497, 5,358,487 and 5,342,305, in which a non-linear compliance curve is obtained from two different sized balloon elements or from use of an inner balloon which bursts at some pressure below the burst pressure of the outer element. The dual concentric balloon structures, are made of materials of quite different strength characteristics and tend to give balloons whose burst strength is little different from to the burst strength of the strongest member element (typically PET or nylon).

SUMMARY OF THE INVENTION

This invention will provide a linear and noncompliant balloon expansion curves. In the case both balloons have almost the same diameters.

In one aspect the invention comprises a laminate balloon comprising at least two layers of separately oriented thermoplastic polymer material, which are coextensive over the body of the balloon. The two layers are preferably made of different polymer materials. Suitably, the layers are sufficiently adherent to each other so that the laminate balloon is a unitary structure even when the balloon is deflated. Most preferably the balloon has an underlying layer made of a low compliant, high strength polymer and an overlying layer of a softer and more flexible polymer material relative to the first polymer material. The inventive balloon structures have an additive burst pressure, meaning that they are stronger than a first single-layer reference balloon corresponding to the underlying polymer layer. The additive strength of the balloons of the invention is exhibited typically by burst strengths greater than the first reference balloon by at least 50%, and commonly at least 75%, of the strength of a second single-layer reference balloon corresponding to the overlying relatively soft flexible polymer layer. Optimal balloons of the invention give burst strengths which exceed the strength of the first reference balloon by about 100% or even more of the strength of the second reference balloon.

The preferred inventive balloons have good flexibility and surface softness, allowing catheters to track down into lesions relatively easily, good puncture resistance, good abrasion resistance and good refold characteristics, all contributed by the soft material top layer. Furthermore they also have a low compliance profile with a burst strength which exceeds the strongest PET angioplasty balloons currently commercially available.

A second aspect of the invention comprises a preferred method of making a laminate balloon which includes the steps of a) providing a first tubing segment of a first polymer material;

b) stretching the first tubing segment at a first stretch ratio to produce a first stretched tube having an outer diameter;

c) providing a second tubing segment of a second polymer material having an inner diameter greater than the outer diameter of the first stretched tube;

d) inserting the first stretched tube into the second tubing segment;

e) stretching the second tubing segment at a second stretch ratio to produce a second stretched tube, the first and second stretched tubes being brought into direct annular contact during the stretching of said second tubing segment, to form a laminate stretched tubing structure; and f) forming the laminate balloon by pressurizing the laminate stretched tubing structure at a temperature and pressure above ambient so as to expand the laminate stretched tubing structure.

A still further aspect of the invention is an alternative process for forming a laminate balloon which includes the steps of:

a) providing a first tubing segment of a first polymer material;

b) stretching the first tubing segment at a first stretch ratio to produce a first stretched tube;

c) blowing the first stretched tube in a mold to produce a first layer structure, said first layer structure including waist, cone and body portions, the waist portion having an inner diameter;

c) providing a second tubing segment of a second polymer material;

d) stretching the second tubing segment at a second stretch ratio to produce a second stretched tube having an outer diameter less than the inner diameter of the waist portion of said first layer structure;

e) inserting the second stretched tube into the first layer structure and f) forming the laminate balloon by pressurizing the second stretched tube at a temperature and pressure above ambient to expand the second layer tube, forming a second layer which is in direct annular contact with the first layer structure.

Balloons of the invention ordinarily have generally linear compliance curves, however, if desired, the balloons can be provided with stepped compliance curves can be prepared by use of a post-blowing annealing process to shrink the balloon.

Further aspects of the invention will become apparent from the following description, claims and drawings.

BRIEF DESCRIPTION OF THE DRAWINGS

FIGS. 1–5 depict various stages in the preferred process for forming a balloon of the invention.

DETAILED DESCRIPTION OF THE PREFERRED EMBODIMENTS

In the preferred embodiments the balloon is formed of two layers of different polymer material, one of which is a low compliant, high strength thermoplastic polymer and the other of which is a relatively soft and flexible polymer material. However, other combinations of polymer materials can also be used, including dual layers of the same polymer material. Furthermore, balloons of the invention can also be prepared using more than two laminae without departing from the principles of the invention hereof.

The materials used for strong layer are low compliant, high strength thermoplastic polymers. Suitably the balloon polymer is poly(ethylene terephthalate) (PET) of initial intrinsic viscosity of at least 0.5, more preferably 0.7–1.3, as reported by the polymer manufacturer. Other high strength polyester materials, such as poly(ethylene napthalenedicarboxylate) (PEN); polyamides such as nylon 11, nylon 12 and aromatic/aliphatic polyamides; thermoplastic polyimides; liquid crystal polymers and high strength engineering thermoplastic polyurethanes such as Isoplast 301 sold by Dow Chemical Co., are considered suitable alternative materials. Physical blends and copolymers of such materials may also be used. Examples of thermoplastic polyimides are described in T. L. St. Clair and H. D. Burks, "Thermoplastic/Melt-Processable Polyimides," NASA Conf. Pub. #2334 (1984), pp. 337–355. A suitable thermoplastic polyimide is described in U.S. Pat. No. 5,096,848 and is available commercially under the tradename Aurum® from Mitsui Toatsu Chemicals, Inc., of Tokyo, Japan. Examples of liquid crystal polymers include the products Vectra® from Hoechst Celanese, Rodrun® from Unitika, LX or HX series polymers from DuPont and Xydar from Amoco. Suitably the liquid crystal polymer materials are blended with another thermoplastic polymer such as PET.

The soft materials used for soft and flexible layer are suitably thermoplastic elastomers, especially segmented polyester/ether block copolymers, such as available under the trademarks Arnitel® and Hytrel®; flexible polyurethanes, such as sold under the trademark Pellethane®; and polyamide/ether block copolymers, such as sold under the Pebax® trademark.

The preferred balloons of the invention are polyester/polyether segmented block copolymers. Such polymers are made up of at least two polyester and at least two polyether segments.

The polyether segments of the polyester/polyether segmented block copolymers are aliphatic polyethers having at least 2 and no more than 10 linear saturated aliphatic carbon atoms between ether linkages. More preferably the ether segments have 4–6 carbons between ether linkages, and most preferably they are poly(tetramethylene ether) segments. Examples of other polyethers which may be employed in place of the preferred tetramethylene ether segments include polyethylene glycol, polypropylene glycol, poly(pentamethylene ether) and poly(hexamethylene ether). The hydrocarbon portions of the polyether may be optionally branched. An example is the polyether of 2-ethylhexane diol. Generally such branches will contain no more than two carbon atoms. The molecular weight of the polyether segments is suitably between about 400 and 2,500, preferably between 650 and 1000.

The polyester segments are polyesters of an aromatic dicarboxylic acid and a two to four carbon diol. Suitable dicarboxylic acids used to prepare the polyester segments of the polyester/polyether block copolymers are ortho-, metaor para-phthalic acid, napthalenedicarboxylic acid or meta-terphenyl-4,4'-dicarboxylic acids. Preferred polyester/polyether block copolymers are poly(butylene terephthalate)-block-poly(tetramethylene oxide) polymers such as Arnitel EM 740, sold by DSM Engineering Plastics. Hytrel polymers, sold by DuPont which meet the physical and chemical specifications set out herein can also be used.

Polyamide/polyether block copolymers may also be used as the soft layer polymer. The polyamide/polyether block copolymers are commonly identified by the acronym PEBA (polyether block amide). The polyamide and polyether segments of these block copolymers may be linked through amide linkages, however, most preferred are ester linked segmented polymers, i. e. polyamide/polyether polyesters. Such polyamide/polyether/polyester block copolymers are made by a molten state polycondensation reaction of a dicarboxylic polyamide and a polyether diol. The result is a short chain polyester made up of blocks of polyamide and polyether. The polyamide and polyether blocks are not miscible. Thus the materials are characterized by a two phase structure: one is a thermoplastic region that is primarily polyamide and the other is elastomer region that is rich in polyether. The polyamide segments are semicrystalline at room temperature. The generalized chemical formula for these polyester polymers may be represented by the following formula:

in which PA is a polyamide segment, PE is a polyether segment and the repeating number n is between 5 and 10.

The polyamide segments are suitably aliphatic polyamides, such as nylons 12, 11, 9, 6, 6/12, 6/11, 6/9, or 6/6. Most preferably they are nylon 12 segments. The polyamide segments may also be based on aromatic polyamides but in such case significantly lower compliance characteristics are to be expected. The polyamide segments are relatively low molecular weight, generally within the range of 500–8,000, more preferably 2,000–6,000, most preferably about 3,000–5,000.

The polyether segments are the same as previously described for the polyester/polyether segmented block copolymers block copolymers useful in the invention.

The weight ratio of polyamide to polyether in the polyamide/polyether polyesters used in the invention desirably should be in the range of 50/50 to 95/5, preferably between 60/30 and 95/5, more preferably, between 70/30 and 92/8.

Polyamide/polyether polyesters are sold commercially under the Pebax® trademark by Atochem North America, Inc., Philadelphia Pa. Examples of suitable commercially available polymers are the Pebax®33 series polymers with hardness 60 and above, Shore D scale, especially Pebax®7233, 7033 and 6333. These polymers are made up of nylon 12 segments and poly(tetramethylene ether) segments in different weight ratios and segment lengths.

It is also possible to use other PEBA polymers with the physical properties specified herein and obtain similar compliance, strength and softness characteristics in the finished balloon.

It is preferred that the block copolymers have a hardness, Shore D scale, of at least 60 and a flexural modulus of no more than about 150,000, in order to obtain optimal strength, compliance and softness characteristics. Preferably the Shore D hardness is in the range of 65–75 and the flexural modulus is in the range of 50,000–120,000. The preferred polymers useful in the invention are also characterized by a high ultimate elongation of about 300% or higher and an ultimate tensile strength of at least 6,000 psi.

The preferred process of forming balloons of the invention will be described with reference to FIGS. 1–5.

Figure 1:
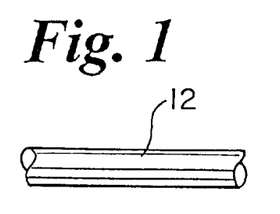
FIG. 1 is a side plan view of a portion of an extruded tubing segment for use in forming a first layer of the inventive balloon according to the preferred process of the invention.
Figure 2:
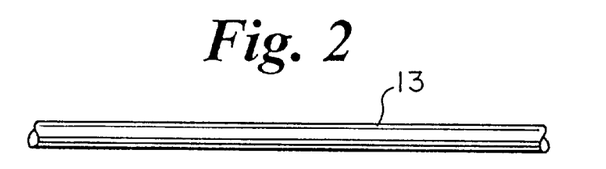
FIG. 2 is a side plan view of the portion of tubing depicted in FIG. 1 after it has been stretched to form the first stretched tube.
Figure 3:
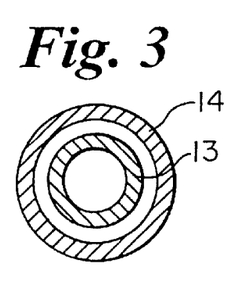
FIG. 3 is a cross-sectional view showing the first stretched tube of FIG. 2 inserted into a second tubing segment.
Figure 4:
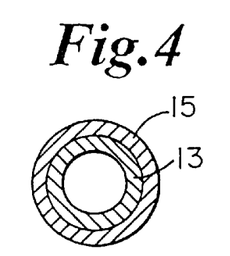
FIG. 4 is a cross-sectional view as in FIG. 3 after the second tubing segment has been stretched down onto the first stretched tube.

Referring to FIG. 1 there is shown an extruded tubing segment 12, preferably made of a strong non-compliant material, such as PET. The tubing segment 12 is stretched longitudinally, typically at an elevated temperature, in conventional manner for PET balloons to produce an elongated stretched tube 13 shown in FIG. 2. The stretch ratio is one which will provide good strength properties in the blown balloon. A typical stretch ratio for a PET material is about 1.5–6 times the length of the original extruded length. An extruded segment 14 of the second polymer material, suitably a polyester/polyether block copolymer, is then provided having an ID greater than the OD of stretched tube 13. Tube 13 is inserted into tube 14 as shown in FIG. 3. Preferably without further stretching of the tube 13, tube 14 is stretched to produce a second stretched tube 15 whose ID is necked down, bringing tube 15 into direct contact with tube 13, as shown in FIG. 4. For the preferred embodiment a "cold-neck" (i.e. at or below ambient temperature) stretch at a ratio of 3–6 may be employed for this step. The composite tubing structure shown in FIG. 4 is then blown at elevated pressure in a manner conventional for single layer balloons, for instance by a process as described in WO 95/22367. The resulting laminate balloon 20, depicted in FIG. 5 has two intimately contacting layers, the inner layer 16 being PET and the outer layer 17 being the polyester/polyether block copolymer material. Although they can easily be pealed apart when the balloon is dissected, layers 16 and 17 are sufficiently adherent that the balloon 20 is a unitary structure even when the balloon is deflated and wrapped onto a catheter.

Figure 5:
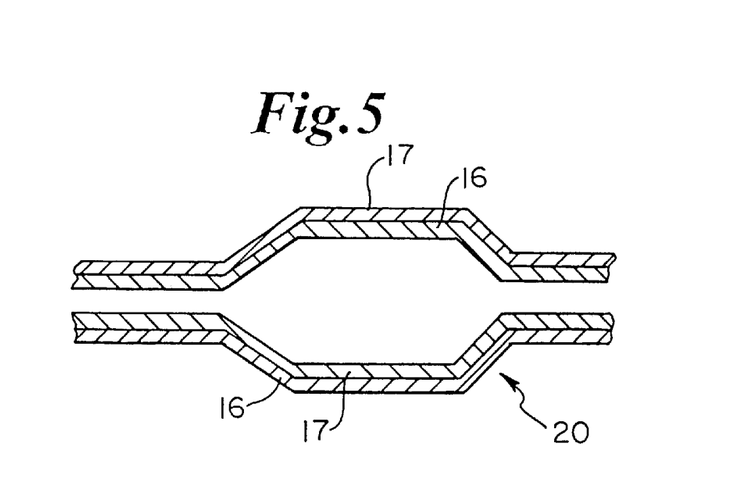
FIG. 5 is a side sectional view of a balloon of the invention.

By this process, and unlike balloons formed from coextruded tubing, the layers 16 and 17 of balloon 20 have been formed with separate stretch ratios applied to the tubes 12 and 14 so that optimal strength properties can be obtained from both layers.

Multi-laminate balloon structures having three or more laminae can be prepared, for instance, by the additional steps of inserting a composite tubing structure of FIG. 4 into a third extruded tube which is necked down onto the outer surface of stretched tube 15 before performing the balloon blowing step. Structures with higher numbers of laminae can be prepared by repetition of these additional steps before blowing the balloon. With such multi-layer laminates it may be desirable to further stretch the composite structure of FIG. 4 or any successive composite stretched tubing structure to reduce the thickness of the composite to be blown and achieve a desired hoop expansion ratio.

An alternative, less preferred process for forming a balloon of the invention is illustrated in Example 9.

After being blown, the dual element balloon of the invention may be provided with a stepped compliance curve by annealing the balloon for a short time after blowing at a pressure at or only slightly above ambient and at a temperature which causes the blown balloon to shrink. The process is described in U.S. Pat. No. 5,348,538. However, the balloons of the invention are desirably constructed with a greater difference between the low pressure and high pressure linear regions of the compliance curve so that the transition between the two regions results in a step-up of diameter of the balloon of at least 0.4 mm. This is accomplished by blowing the balloon to the larger diameter and then shrinking to a greater extent than was done in the specific illustrative examples of U.S. Pat. No. 5,348,538. The amount of shrinkage is controlled by the pressure maintained in the balloon during annealing and the temperature and time of the annealing. The annealing pressure is suitably in the range of 0–20, preferably 5–10 psi at 70–100° C. for 3 seconds to 3 hours.

The invention is illustrated by the following non-limiting examples.

EXAMPLE 1

A PET tube was extruded with an inner diameter of 0.0136 inch and an outer diameter of 0.0288 inch from Traytuf7357 (Shell Chemical, Akron) PET resin. The PET tube was stretched to 2.25× its original length (2.25 stretch ratio) at 90° C. The stretched tube was then inserted into a tube of extruded polyester-polyether block copolymer resin (Arnitel EM 740, DSM Engineering Plastics, Evansville Ind.) of 0.0260 inch ID and 0.0340 inch OD. The polyester-polyether resin tube was cold necked (stretched at ambient temperature) at 4.0 stretch ratio over the PET tube, without further stretching of the PET tube. The resulting coaxially arranged tube assembly was then inserted into a 3.0 mm balloon mold and blown. The mold temperature was 97° C. and the blowing pressure was 350 psi with 30 gms tension applied during the blowing process. The measured balloon double wall thickness (i.e. two layers of PET and two layers of polyester-polyether) was 0.00145 inch, corresponding to a single wall thickness (one layer each of PET and polyester-polyether) of 0.00073 inch. The compliance curve showed balloon growth from 8 to 18 atm of 2.6%, and 6.25% from 8 to 28 atm. The balloon burst pressure was 529 psi (36 atm). When the balloons prepared in this manner were dissected, the double wall thickness of the PET element was 0.00085 inch and of the polyester-polyether element was 0.0006 inch.

EXAMPLE 2

Reference Example

An extruded tube of the same Arnitel EM 740 polyester/polyether resin with the same dimension used in Example 1 was made into a single layer balloon having a double wall thickness 0.0006 inch by stretching and blowing the balloon under similar conditions to those of Example 1. The burst pressure of this balloon was 147 psi (10 atm).

EXAMPLE 3

Reference Example

A PET tube with the same dimension as used in Example 1 was made into a single layer balloon having a double wall thickness of 0.00085 inch by stretching and blowing under similar conditions as in Example 1. The burst pressure of this balloon was 338 psi. (23 atm).

Comparison of the burst strengths of the two reference balloons produced in Examples 2 and 3 with the burst strength of the inventive balloon of Example 1 shows that the strength of the inventive balloon was more than the sum of the strengths of the two reference balloons.

EXAMPLE 4

A PET tube was extruded with an inner diameter of 0.0134 inch and an outer diameter of 0.0325 inch from Traytuf7357 PET resin. The PET tube was stretched at a 2.25 stretch ratio at 90° C. The stretched tube was then inserted into a tube of extruded Arnitel EM 740 polyester-polyether block copolymer resin. The extruded tube had dimensions of 0.0245 inch ID and 0.0405 inch OD. The polyester-polyether resin tube was stretched at ambient temperature at 4.0 stretch ratio over the PET tube, without further stretching of the PET tube. The resulting coaxially arranged tube assembly was then inserted into a balloon 3.0 mm mold and blown. The mold temperature was 97° C. and the blowing pressure was 460 psi with 150 gms tension applied during the blowing process. The measured balloon double wall thickness was 0.0016 inch, corresponding to a single wall thickness (one layer each of PET and polyester-polyether) of 0.0008 inch. The compliance curve showed balloon growth from 8 to 18 atm of 4%, and 9% from 8 to 28 atm. The balloon burst pressure was 426 psi (29 atm). When similarly prepared balloons were dissected, the double wall thickness of the PET element was 0.0009 inch and of the polyester-polyether element was 0.0008 inch.

EXAMPLE 5

Figure 6:
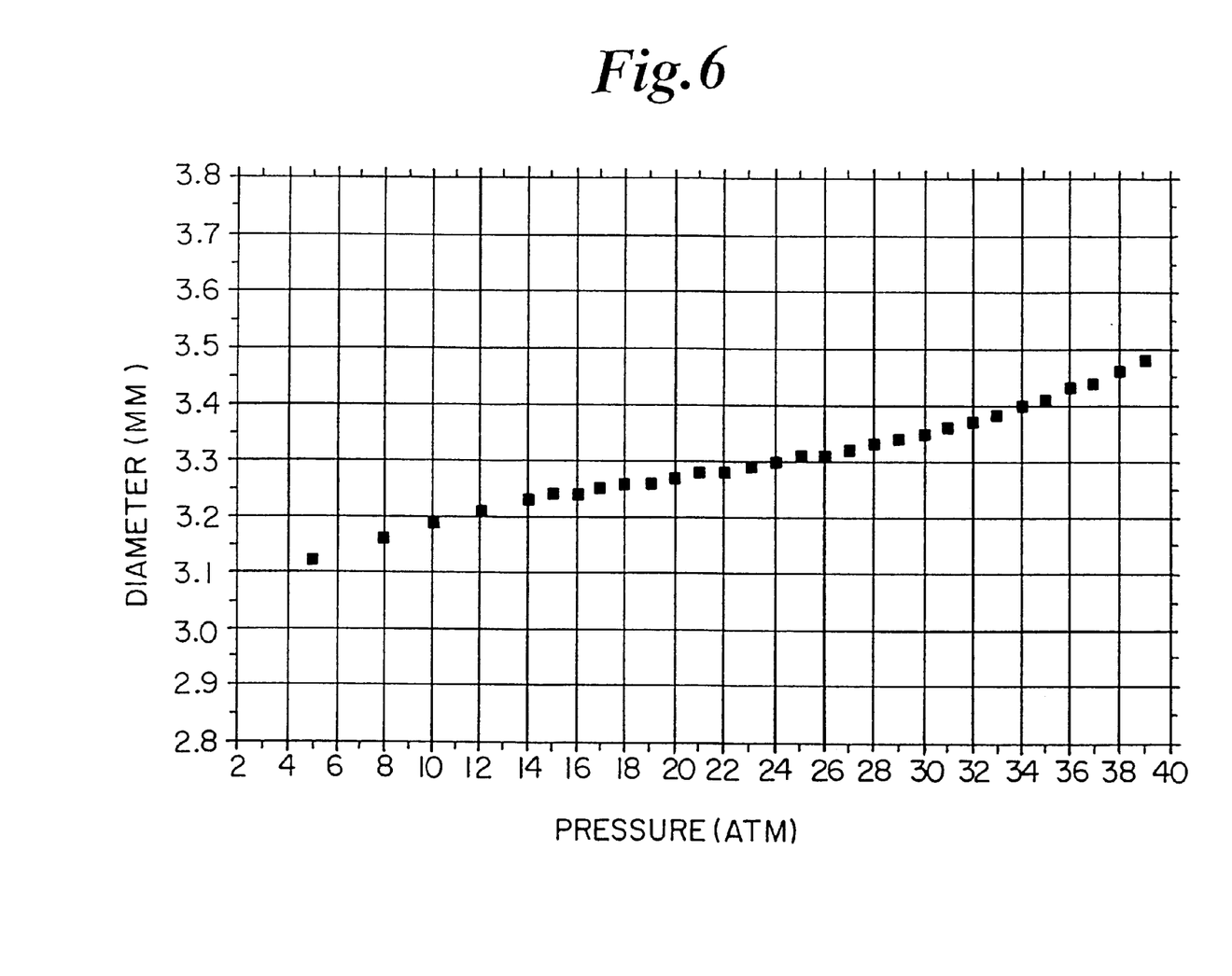
FIG. 6 is a graph of the compliance curve of a balloon prepared in accordance with Example 5.

A PET tube was extruded with an inner diameter of 0.0147 inch and an outer diameter of 0.0291 inch from Traytuf7357 PET resin. The PET tube was stretched at a 2.25 stretch ratio at 90° C. The stretched tube was then inserted into a tube of extruded Arnitel EM 740 polyester-polyether block copolymer resin. The extruded tube had dimensions of 0.026 inch ID and 0.043 inch OD. The polyester-polyether resin tube was stretched at ambient temperature at 4.0 stretch ratio over the PET tube, without further stretching of the PET tube. The resulting coaxially arranged tube assembly was then inserted into a balloon 3.25 mm mold and blown. The mold temperature was 97° C. and the blowing pressure was 500 psi with 600 gms tension applied during the blowing process. The measured balloon double wall thickness was 0.0022 inch. The PET layer double wall thickness was 0.0012 inch and the Arnitel layer double wall thickness was 0.0010 inch. The compliance curve showed balloon growth from 8 to 18 atm of 3%, and 5% from 8 to 28 atm. The balloon burst pressure was 573 psi (39 atm). The compliance curve for this balloon is shown in FIG. 6.

EXAMPLE 6

Reference Example

A tube of Arnitel EM 740 resin with the same dimensions as example 2 was made into a single balloon with double wall thickness 0.0007 inch. The burst pressure of the resulting balloon was 221 psi (15 atm).

EXAMPLE 7

Reference Example

A PET tube with the same dimensions as example 3 was made into a single layer balloon with double wall thickness 0.0008 inch. The burst pressure was 330 psi (22 atm).

EXAMPLE 8

Figure 7:
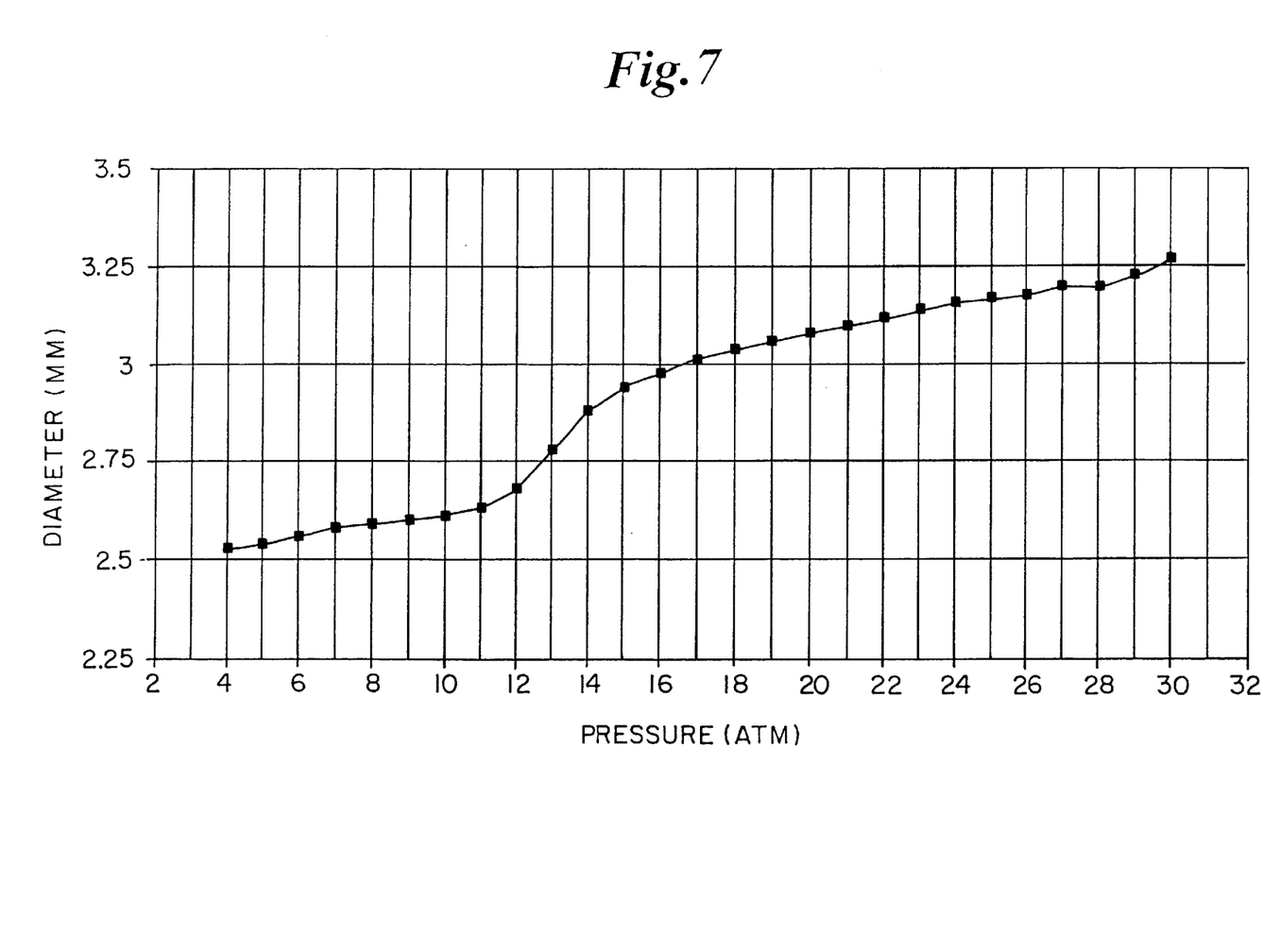
FIG. 7 is a graph of the compliance curve of a balloon prepared in accordance with Example 8.

A PET tube of 0.0147 inch ID and 0.0275 inch OD was extruded from Traytuf7357 PET resin. The PET tube was stretched at a 2.25 ratio at 90° C. The stretched tube was then inserted into a tube of extruded Arnitel EM 740 resin. Then, the Arnitel tube was stretched at ambient temperature over the PET tube at a 4.0 stretch ratio, without further stretching the PET tube. The combined tube was then inserted into a mold with body dimension of 3.0 mm. The mold process was similar to that described in WO95/22367, using a mold temperature of 97° C. and blowing pressure/tension settings (psi/gms) of 530/40, 150/40 and 580/100, respectively, to blow the proximal, body and distal portions of the balloon respectively. The balloon was then shrunk by annealing at 82° C. for 2 hours at 5 psi inflation pressure. The balloon double wall thickness was 0.0018 inch. The balloon had a hybrid or step compliance curve as demonstrated in FIG. 7. The average balloon burst pressure for 3 balloons prepared in this manner was 417 psi (28.5 atm).

EXAMPLE 9

This example illustrates an alternative laminate balloon blowing procedure of the invention and produces a balloon in which the soft flexible polymer is the under layer.

Extruded tubes of PET having dimensions of 0.0136 ID and 0.0288 OD and Arnitel EM 740 having dimensions of 0.0210 ID and 0.0370 OD were used in this example. Single layer PET balloons were prepared by stretching the PET tubes at 2.25 stretch ratio and then blowing the stretched tubes in a 2.8 mm mold using a mold temperature of 97° C. and blowing pressure/tension settings (psi/gms) of 210/20, 100/20 and 210/20, respectively, to blow the proximal, body and distal portions of the balloons respectively. The Arnitel EM 740 tubes were stretched at ambient temperature at a 4.0 stretch ratio and each inserted into a PET balloon, still in the mold. The Arnitel tubing was blown at 80° C. and 400 psi pressure without applying tension, yielding laminate balloons which had an average double wall thickness of 0.0023 inch and an average burst pressure of 398 psi (27 atm).

Balloons of the invention may be prepared for use on medical devices in various interventional medical specialties including cardiology, gastroenterology, pulmonary medicine, radiology, urology and vascular surgery. Examples of useful applications include catheters used in coronary and vascular percutaneous transluminal angioplasty, catheters used for ultrasound or laser imaging systems, catheters used to deliver and implant vascular prostheses, devices used to diagnose and treat gastrointestinal disorders, biliary interventional products used in endoscopic procedures in the gall bladder and bile ducts, and prostrate dilatation catheters. Depending on the particular application, the balloons may be prepared with a wide range of inflated diameters, typically in the range of 1 mm to about 30 mm, and more typically 1.5 mm to about 20 mm, with typical lengths ranging from 5 mm to about 100 mm.

Although the present invention has been described in terms of specific embodiments, it is anticipated that alterations and modifications thereof will no doubt be come apparent to those skilled in the art. It is therefore intended that the following claims be interpreted as covering all such alterations and modifications as fall within the true spirit and scope of the invention.

What is claimed is:

1. A process for producing a laminate balloon for mounting on a catheter, the process comprising the steps of:
    a) providing a first tubing segment of a first polymer material;
    b) stretching the first tubing segment at a first stretch ratio to produce a first stretched tube having an outer diameter;
    c) providing a second tubing segment of a second polymer material having an inner diameter greater than the outer diameter of the first stretched tube;
    d) inserting the first stretched tube into the second tubing segment;
    e) stretching the second tubing segment at a second stretch ratio to produce a second stretched tube, the first and second stretched tubes being brought into direct annular contact during the stretching of said second tubing segment, to form a laminate stretched tubing structure; and
    f) forming the laminate balloon by pressurizing the laminate stretched tubing structure at a temperature and pressure above ambient so as to expand the laminate stretched tubing structure.

2. A process as in claim 1 wherein the first and second polymer materials are different polymer materials.

3. A process as in claim 2 wherein the first polymer material is a low compliant, high strength polymer and the second polymer is a softer and more flexible polymer material relative to the first polymer material.

4. A process as in claim 3 wherein the first polymer material is selected from the group consisting of polyesters, polyamides, thermoplastic polyimides, liquid crystal polymers and high strength engineering thermoplastic polyurethanes and the second polymer material is a thermoplastic elastomer.

5. A process as in claim 4 wherein said thermoplastic elastomer is a polyester/polyether segmented block copolymer.

6. A process as in claim 1 wherein the first and second stretch ratios have different values.

7. A process as in claim 6 wherein in said balloon forming step (f) said laminate stretched tubing structure is expanded to a preselected diameter.

8. A process as in claim 7 wherein said balloon forming step (f) is performed in a mold.

9. A process as in claim 7 wherein said first and second stretch ratios are individually selected to produce in said laminate balloon at least one preselected strength or compliance characteristic.

10. A process as in claim 9 wherein said first polymer material is a low compliant, high strength polymer, said second polymer is a softer and more flexible polymer material relative to the first polymer material, whereby said laminate balloon comprises an underlayer of said first polymer and an overlayer of said second polymer material, said at least one preselected characteristic includes a laminate balloon burst strength value greater than the burst strength of a first reference balloon of said first polymer formed at a wall thickness, a stretch ratio and a hoop expansion ratio substantially the same as the wall thickness, stretch ratio and hoop expansion ratio of said laminate balloon underlayer.

11. A process as in claim 10 wherein said laminate balloon burst strength value exceeds the burst strength of the first reference balloon by an amount which is at least 50% of the burst strength of a second reference balloon of said second polymer formed at a wall thickness, a stretch ratio and a hoop expansion ratio substantially the same as the wall thickness, stretch ratio and hoop expansion ratio of said laminate balloon overlayer.

12. A process as in claim 11 wherein said laminate balloon burst strength value exceeds the burst strength of said first reference balloon by an amount which is at least 75% of the burst strength of said second reference balloon.

13. A process for forming a laminate balloon which includes the steps of:
    a) providing a first tubing segment of a first polymer material;

b) stretching the first tubing segment at a first stretch ratio to produce a first stretched tube;
c) blowing the first stretched tube in a mold to produce a first layer structure, said first layer structure including waist, cone and body portions, the waist portion having an inner diameter;
d) providing a second tubing segment of a second polymer material;
e) stretching the second tubing segment at a second stretch ratio to produce a second stretched tube having an outer diameter less than the inner diameter of the waist portion of said first layer structure;
f) inserting the second stretched tube into the first layer structure and
g) forming the laminate balloon by pressurizing the second stretched tube at a temperature and pressure above ambient to expand the second layer tube, forming a second layer which is in direct annular contact with the first layer structure.

* * * * *